United States Patent
Valvano et al.

(10) Patent No.: US 11,686,800 B2
(45) Date of Patent: Jun. 27, 2023

(54) CORRECTION OF MAGNETIC RESONANCE IMAGES USING SIMULATED MAGNETIC RESONANCE IMAGES

(71) Applicant: KONINKLIJKE PHILIPS N.V., Eindhoven (NL)

(72) Inventors: Giuseppe Valvano, Best (NL); Elwin de Weerdt, Best (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/599,216

(22) PCT Filed: Apr. 1, 2020

(86) PCT No.: PCT/EP2020/059225
§ 371 (c)(1),
(2) Date: Sep. 28, 2021

(87) PCT Pub. No.: WO2020/201336
PCT Pub. Date: Oct. 8, 2020

(65) Prior Publication Data
US 2022/0179028 A1   Jun. 9, 2022

(30) Foreign Application Priority Data

Apr. 1, 2019  (EP) .................................. 19166575

(51) Int. Cl.
*G01R 33/56*       (2006.01)
*A61B 5/055*       (2006.01)
(Continued)

(52) U.S. Cl.
CPC .......... *G01R 33/5608* (2013.01); *A61B 5/055* (2013.01); *G01R 33/50* (2013.01); *G06T 11/006* (2013.01)

(58) Field of Classification Search
CPC .... A61B 5/055; G01R 33/50; G01R 33/5608; G06T 11/006
See application file for complete search history.

(56) References Cited

U.S. PATENT DOCUMENTS 9,052,409 B2 *  6/2015  Prange ..................... G01V 3/32
10,429,475 B2 * 10/2019 Polimeni .............. G01R 33/385
(Continued)

FOREIGN PATENT DOCUMENTS

WO    2018036986 A1    3/2018

OTHER PUBLICATIONS

Fuderer, M. et al., "SENSE reconstruction using feed forward regularization", International Society for Magnetic Resonance in Medicine, ISMRM, 12th Scientific Meeting and Exhibition, Kyoto, Japan, (May 1, 2004), p. 2130.
(Continued)

*Primary Examiner* — Gregory H Curran

(57) ABSTRACT

Disclosed is a medical imaging system (100, 300). The execution of machine executable instructions (120) causes a processor (104) to: receive (200) measured magnetic resonance imaging data (122) descriptive of a first region of interest (307) of a subject (318); receive (202) a B0 map (124), a T1 map (126), a T2 map (128), and a magnetization map (130) each descriptive of a second region of interest (309) of the subject; receive (204) pulse sequence commands (132); calculate (206) a simulated magnetic resonance image (136) of an overlapping region of interest (311) using at least the B0 map, the T1 map, the T2 map, the magnetization map, and the pulse sequence commands as input to a Bloch equation model (134); and reconstruct (208) a corrected magnetic resonance image from the measured magnetic resonance imaging data for the overlapping region of interest by solving an inverse problem. The inverse problem comprises an optimization of a cost function and a
(Continued)

regularization term formed from the simulated magnetic resonance image.

14 Claims, 10 Drawing Sheets

(51) Int. Cl.
  *G01R 33/50* (2006.01)
  *G06T 11/00* (2006.01)

(56) References Cited

U.S. PATENT DOCUMENTS

| | | |
|---|---|---|
| 2005/0270024 A1 | 12/2005 | Lin |
| 2009/0161932 A1 | 6/2009 | Chen |
| 2013/0181711 A1 | 7/2013 | Chaari et al. |
| 2014/0239949 A1 | 8/2014 | Huang et al. |
| 2014/0316250 A1* | 10/2014 | Ahmad .................. G01R 33/56 600/416 |
| 2016/0124064 A1 | 5/2016 | De Weerdt |
| 2018/0276852 A1 | 9/2018 | Chen |
| 2019/0227138 A1 | 7/2019 | De Weerdt |

OTHER PUBLICATIONS

International Search Report for PCT/EP2020/059225 filed Apr. 1, 2020.

Lin et al "Parallel Imaging Reconstruction Using Automatic Regularization" Magnetic Resonance in Med. vol. 51 p. 559-567 (2004).

Ma D, Gulani V, Seiberlich N, Liu K, Sunshine JL, Duerk JL, Griswold MA. Magnetic resonance fingerprinting. Nature 2013;495:187-192.

Julian Rasch et al "Dynamic MRI Reconstruction from Undersampled Data with an Anatomical Prescan" 2018 Inverse Problems 34 074001.

Heigl, Herbert, CUDA powered MRI reconstruction with variational constraints, Master Thesis, Graz University of Technology, Jan. 2019.

Asslaender, Jakob, et al., Low Rank Alternating Direction Method of Multipliers Reconstruction for MR Fingerprinting, Magnetic Resonance in Medicine, Willey, Jan. 22, 2017, vol. 79, pp. 83-96.

* cited by examiner

CORRECTION OF MAGNETIC RESONANCE IMAGES USING SIMULATED MAGNETIC RESONANCE IMAGES

CROSS-REFERENCE TO PRIOR APPLICATIONS

This application is the U.S. National Phase application under 35 U.S.C. § 371 of International Application No. PCT/EP2020/059225, filed on Apr. 1, 2020, which claims the benefit of European Patent Application No. 19166575.1, filed on Apr. 1, 2019. These applications are hereby incorporated by reference herein.

FIELD OF THE INVENTION

The invention relates to magnetic resonance imaging, in particular to image reconstruction for magnetic resonance imaging.

BACKGROUND OF THE INVENTION

A large static magnetic field is used by Magnetic Resonance Imaging (Mill) scanners to align the nuclear spins of atoms as part of the procedure for producing images within the body of a patient. This large static magnetic field is referred to as the B0 field or the main magnetic field. By applying time dependent magnetic field gradients and radio frequency (RF) pulses various quantities or properties of the subject can be measured spatially using MM. However, depending upon the particular imaging protocol there may be various distortions or artifacts present in a reconstructed image.

United States Patent application publication US20050270024A1 discloses a method of parallel imaging reconstruction in parallel magnetic resonance imaging reconstruction. Magnetic resonance data is acquired in parallel by an array of separate RF receiver coils. A reconstruction method based on Tikhonov regularization is presented to reduce the SNR loss due to geometric correlations in the spatial information from the array coil elements. In order to reduce the noise amplification of the reconstruction so-called "g-factor", reference scans are utilized as a priori information of the final reconstructed image to provide regularized estimates for the reconstruction using the L-curve technique.

SUMMARY OF THE INVENTION

The invention provides for a medical imaging system, a computer program product, and a method in the independent claims. Embodiments are given in the dependent claims.

When there are distortions or artifacts present in a magnetic resonance image, there are various methods which can be used to remove or reduce the distortions or artifacts. Embodiments solve this problem by formulating either the image reconstruction or an image correction for measured magnetic resonance imaging data as an inverse problem (an optimization problem). The inverse problem has a cost function which is dependent upon values taken from a simulated magnetic resonance image.

The simulated magnetic resonance image is calculated using a B0 map, and at least one of a transverse relaxation map and a longitudinal relaxation map, preferably both a T1 map, a T2 map and/or a T2* map, a magnetization map, and pulse sequence commands as input to a Bloch equation model or solver. It appears that the simulated magnetic resonance image can be derived using a B0 map and one of a transverse or a longitudinal relaxation map. The transverse relaxation map may include a T2 map and/or a T2* map. The longitudinal relaxation map includes a T1 map. In the event that image information is dominated by magnetic resonance imaging data at short echo times then transverse relaxations may be neglected. On the other hand, when image information is dominated by contributions for very long repetition times, then longitudinal recovery and hence the longitudinal relaxations may be neglected. The pulse sequence commands may be the same pulse sequence commands that were used to acquire the measured magnetic resonance imaging data. This means that the contrast for the simulated magnetic resonance image and an image reconstructed from the measured magnetic resonance imaging data should be approximately the same. An insight of the present invention is that a simulated magnetic resonance image that is useful as a reference in the optimisation problem can be calculated on the basis of the B0 map and at least one of the longitudinal relaxation map and the transverse relaxation map. The simulated magnetic resonance image may also be free of the artifacts or distortions present in the measured magnetic resonance imaging data. The use of the simulated magnetic resonance image may therefore provide for improved image reconstruction or correction. The B0 map, T1 map, T2 map and magnetization map may come from various sources, however a convenient way of providing these values is via a scan using magnetic resonance imaging fingerprinting.

In one aspect the invention provides for a medical imaging system. The medical imaging system comprises a memory for storing machine-executable instructions and a processor for controlling the medical imaging system. Execution of the machine-executable instructions causes the processor to receive measured magnetic resonance imaging data descriptive of a first region of interest of a subject. The measured magnetic resonance imaging data may for example be in either image or in k-space. Execution of the machine-executable instructions further causes the processor to receive a B0 map, a T1 map, a T2 map, and a magnetization map which are each descriptive of a second region of interest of the subject. The first region of interest of the subject and the second region of interest of the subject both comprise an overlapping region of interest.

Execution of the machine-executable instructions further causes the processor to receive pulse sequence commands configured for controlling a magnetic resonance imaging system to acquire the measured magnetic resonance imaging data. Execution of the machine-executable instructions further causes the processor to calculate a simulated magnetic resonance image of the overlapping region of interest using at least the B0 map, the T1 map, the T2 map, the magnetization map and the pulse sequence commands as input to a Bloch equation model. The Bloch equation model may for example be used to simulate the acquisition of magnetic resonance imaging data.

Execution of the machine-executable instructions further causes the processor to reconstruct a corrected magnetic resonance image from the measured magnetic resonance imaging data for the overlapping region of interest by solving an inverse problem. The inverse problem comprises an optimization of a cost function and a regularization term formed from the simulated magnetic resonance image. In some cases, the cost function and the regularization term will be formulated in image space. In other examples the cost function and the regularization term are formulated in k-space.

A medical imaging system as used herein encompasses both a computer or processing system which is used to perform image processing and various mathematical calculations. A medical imaging system may also comprise other components which are used to acquire the measured magnetic resonance imaging data.

In some examples the first region of interest and the second region of interest could be identical.

In another embodiment the transverse relaxation map includes T2 map and/or a T2* map.

In another embodiment the regularization term is a Tikhonov regularization, The Tikhonov regularization comprises an estimate of a first image magnitude calculated from the corrected magnetic resonance imaging data divided by a second image magnitude calculated from the simulated magnetic resonance image for each voxel of the overlapping region of interest. This embodiment may be beneficial because it may provide for a general means of constructing the corrected magnetic resonance image in various situations.

In another embodiment the inverse problem is an echo planar imaging geometry reconstruction.

In another embodiment the cost function comprises an Euclidean norm of a difference between a distortion operator times the corrected magnetic resonance imaging data and the measured magnetic resonance image. This embodiment can be rephrased as: in another embodiment the cost function comprises an Euclidean norm of a distortion operator times the corrected magnetic resonance imaging data minus the measured magnetic resonance image. This embodiment can be further rephrased as: in another embodiment the cost function comprises the Euclidean norm of the measured magnetic resonance image minus a distortion operator times the corrected magnetic resonance imaging data.

In another embodiment the cost function comprises the Euclidean norm of the difference between a distortion operator times the corrected magnetic resonance imaging data and the measured magnetic resonance image. This embodiment can be rephrased as: in another embodiment the cost function comprises an Euclidean norm of a distortion operator times the corrected magnetic resonance imaging data minus the measured magnetic resonance image. This embodiment can be rephrased as: in another embodiment the cost function comprises an Euclidean norm of the measured magnetic resonance image minus a distortion operator times the corrected magnetic resonance imaging data. This operation may be performed on a per voxel basis.

In another embodiment the inverse problem is a parallel imaging unfolding. This embodiment may be beneficial because it may provide for a general means of unfolding of parallel image magnetic resonance images. In one example the parallel image unfolding is a SENSE unfolding.

In another embodiment the cost function comprises an Euclidean norm of a difference between a folding operator times a coil sensitivity map times the corrected magnetic resonance image and the measured magnetic resonance image. This embodiment can be rephrased as: in another embodiment the cost function comprises an Euclidean norm of a folding operator times a coil sensitivity map times the corrected magnetic resonance image minus the measured magnetic resonance image. This embodiment can be rephrased as: in another embodiment the cost function comprises an Euclidean norm of a folding operator times a coil sensitivity map times the corrected magnetic resonance image minus the measured magnetic resonance image. This may for example be performed using values on a per voxel basis. This may provide for a general means of doing parallel image unfolding.

In another embodiment the inverse problem is a compressed sensing in combination with a parallel imaging-based reconstruction.

In another embodiment the cost function comprises an Euclidean norm of an under sampled Fourier transform×a coil sensitivity map×the corrected magnetic resonance image–the measured magnetic resonance image. This embodiment may be beneficial because it may provide a means of formulating the inverse problem for compressed sensing and parallel imaging-based reconstruction.

In another embodiment the B0 map, the T1 map, the T2 map, and a magnetization map have a first resolution. Magnetic resonance imaging has a second resolution. The first resolution is lower than the second resolution. This embodiment may be beneficial because very rough values of the B0 map, the T1 map, the T2 map, and a magnetization map may be useful in formulating the cost function.

In another embodiment execution of the machine-executable instructions further cause the processor to perform a multi-planar reformatting of the B0 map, the T1 map, the T2 map, and the magnetization map to make a geometric match to the measured magnetic resonance imaging data before calculating the simulated magnetic resonance image. In image space this may be interpolating the various values of voxels. In k-space this may include resampling it to the same sampling pattern as in the measured magnetic resonance imaging data.

In another embodiment execution of the machine-executable instructions further cause the processor to receive magnetic resonance fingerprint data acquired according to a magnetic resonance fingerprinting protocol. The magnetic resonance fingerprint data is descriptive of the second region of interest. Execution of the machine-executable instructions further cause the processor to reconstruct at least one of the B0 map, the T1 map, the T2 map, and a magnetization map from the magnetic resonance fingerprinting magnetic resonance imaging data using a magnetic resonance fingerprinting dictionary according to the magnetic resonance imaging protocol.

This embodiment may be beneficial because the B0 map, the T1 map, the T2 map, and a magnetization map may all be calculated relatively quickly using magnetic resonance fingerprinting. All the various maps may be reconstructed using magnetic resonance fingerprinting, however some of the maps may be obtained from other sources or imaging protocols.

In another embodiment execution of the machine-executable instructions further cause the processor to receive magnetic resonance imaging data according to a magnetic resonance imaging protocol. The magnetic resonance imaging data is descriptive of the first region of interest. Execution of the machine-executable instructions further cause the processor to reconstruct a magnetic resonance image from the magnetic resonance imaging data. In some cases, the measured magnetic resonance imaging data is used directly in a cost function. In other examples the measured magnetic resonance image is used instead.

In another embodiment the medical imaging system further comprises a magnetic resonance imaging system. The memory further contains magnetic resonance imaging pulse sequence commands configured for acquiring the magnetic resonance imaging data. The memory further contains magnetic resonance fingerprinting pulse sequence commands configured for acquiring the magnetic resonance fingerprint data according to the magnetic resonance fingerprinting protocol. Execution of the machine-executable instructions causes the processor to control the magnetic resonance imaging system with the magnetic resonance fingerprinting pulse sequence commands to acquire the magnetic resonance fingerprint data. Execution of the machine-executable instructions causes the processor to control the magnetic resonance imaging system with the magnetic resonance imaging pulse sequence commands to acquire the measured magnetic resonance imaging data.

In another aspect the invention provides for a computer program product comprising machine-executable instructions for execution by a processor controlling a medical imaging system. Execution of the machine-executable instructions causes the processor to receive measured magnetic resonance imaging data descriptive of a first region of interest of a subject. Execution of the machine-executable instructions further cause the processor to receive a B0 map, a T1 map, a T2 map, and a magnetization map which are each descriptive of a second region of interest of the subject. The first region of interest of the subject and the second region of interest of the subject both comprise an overlapping region of interest. Execution of the machine-executable instructions further cause the processor to receive pulse sequence commands configured for controlling a magnetic resonance imaging system to acquire the magnetic resonance imaging data.

Execution of the machine-executable instructions further cause the processor to calculate a simulated magnetic resonance image of the overlapping region of interest using at least the B0 map, the T1 map, the T2 map, the magnetization map, and the pulse sequence commands as input to a Bloch equation model. Execution of the machine-executable instructions further cause the processor to reconstruct a corrected magnetic resonance image from the measured magnetic resonance imaging data for the overlapping region of interest by solving an inverse problem. The inverse problem comprises an optimization of a cost function and a regularization term formed from the simulated magnetic resonance image. The advantages of this have been previously discussed.

In another aspect the invention further provides for a method of operating a medical imaging system. The method comprises receiving measured magnetic resonance imaging data descriptive of a first region of interest of the subject. The method further comprises receiving a B0 map, a T1 map, a T2 map, and a magnetization map each descriptive of a second region of interest of the subject. The first region of interest of the subject and the second region of interest of the subject both comprise an overlapping region of interest. The method further comprises receiving pulse sequence commands configured for controlling the magnetic resonance imaging system to acquire the magnetic resonance imaging data.

The method further comprises calculating a simulated magnetic resonance image of the overlapping region of interest using at least the B0 map, the T1 map, the T2 map, the magnetization map, and the pulse sequence commands as input to a Bloch equation model. The method further comprises reconstructing a corrected magnetic resonance image from the measured magnetic resonance imaging data for the overlapping region of interest by solving an inverse problem. The inverse problem comprises an optimization of a cost function and a regularization term formed from the simulated magnetic resonance image. The advantages of this have been previously discussed.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid-state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object-oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data or Magnetic Resonance Imaging data is defined herein as being the recorded measurements of radio frequency signals emitted by atomic spins using the antenna of a Magnetic resonance apparatus during a magnetic resonance imaging scan. Magnetic Resonance Fingerprint (MRF) data is an example of magnetic resonance data. Magnetic resonance data is an example of medical image data. A Magnetic Resonance Imaging (MM) image or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
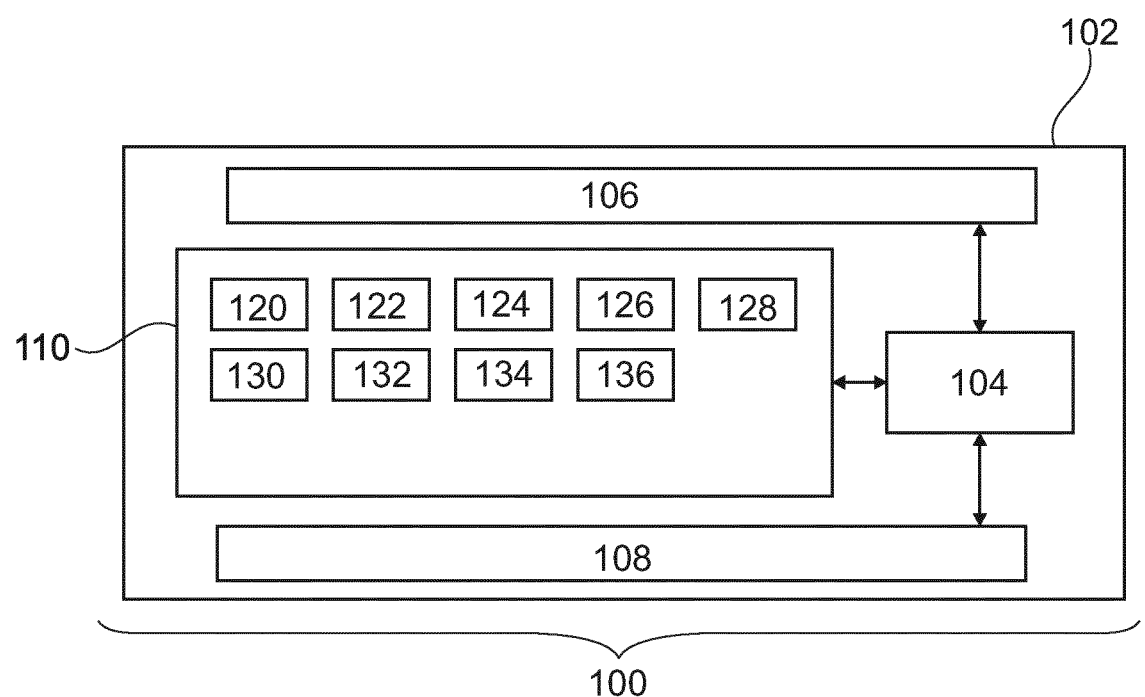
FIG. 1 illustrates an example of a medical imaging system.

FIG. 1 illustrates of an example of a medical imaging system 100. The medical imaging system 100 depicted in FIG. 1 comprises a computer 102. The computer comprises a processor 104. The processor 104 is intended to represent one or more processors or processing cores. The processors 104 may also be distributed amongst multiple computer systems 102. There is a hardware interface 106 which is connected to the processor 104. The hardware interface 106 may for example be used for forming a network connection with other computer systems, controlling other components of the medical imaging system 100, or interfacing with other equipment. There is also a user interface 108 which is also connected to the processor 104. There is a memory 110 connected to the processor 104 also. The memory 110 may be any combination of memory which is accessible to the processor 104. This may include such things as main memory, cached memory, and also non-volatile memory such as flash RAM, hard drives, or other storage devices. In some examples the memory 110 may be considered to be a non-transitory computer-readable medium.

The memory 110 is shown as containing machine-executable instructions 120. The machine-executable instructions 120 enable the processor to control other components of the medical imaging system 100 via the hardware interface 106. Additionally, the machine-executable instructions 120 may allow the processor 104 to perform various data processing and image processing calculations and techniques. The memory 110 is further shown as containing measured magnetic resonance imaging data 122. The memory 110 is further shown as containing a B0 map 124, a T1 map 126, a T2 map 128 and a magnetization map 130. These various maps 124, 126, 128, 130 may be from a magnetic resonance fingerprinting acquisition.

The memory 110 is further shown as containing a Bloch equation model 134. The Bloch equation model 134 enables the simulated acquisition of magnetic resonance imaging data. The memory 110 is shown as containing a simulated magnetic resonance image 136. The Bloch equation model 134 may for example be used for calculating simulated magnetic resonance imaging data which is not depicted.

The memory 110 is further shown as containing the corrected magnetic resonance image 138 that was reconstructed from the measured magnetic resonance imaging data 122. This is performed using the simulated magnetic resonance image 136 to form a regularization term which is used in a cost function. The optimization is then used to reconstruct the corrected magnetic resonance image 138.

Figure 2:
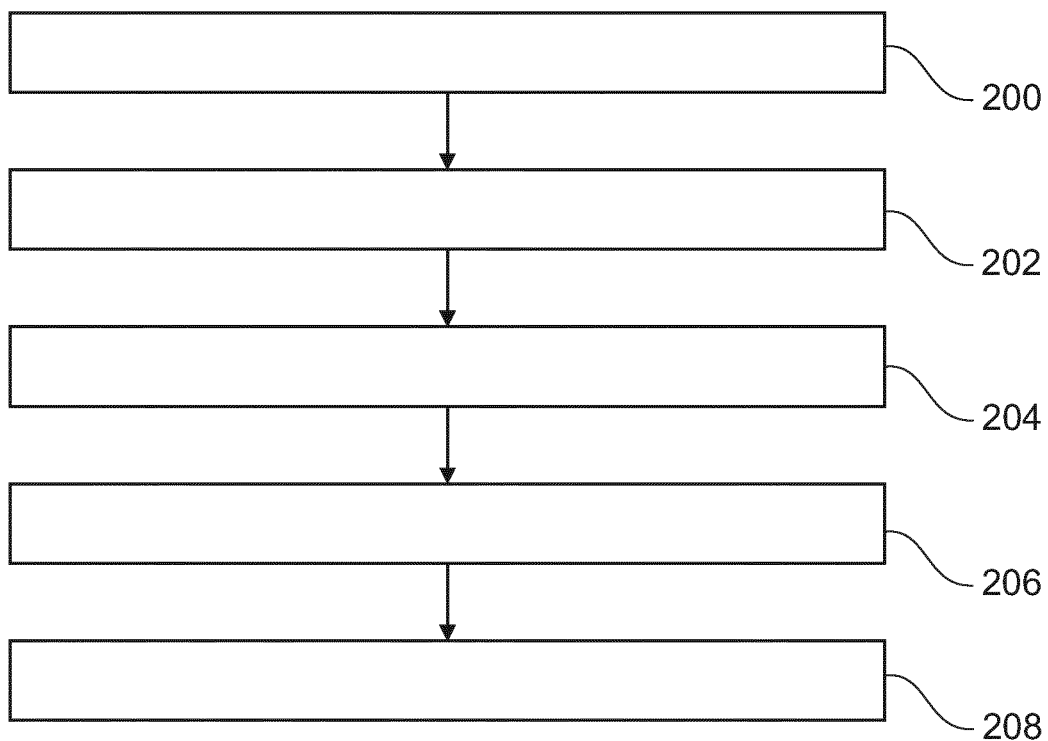
FIG. 2 shows a flow chart which illustrates a method of using the medical imaging system of FIG. 1.

FIG. 2 shows a flowchart illustrating a method of operating the medical imaging system 100 of FIG. 1. First in step 200 the measured magnetic resonance imaging data 122 is received. The measured magnetic resonance imaging data is descriptive of a first region of interest of a subject. Next in step 202 the B0 map 124, the T1 map 126, the T2 map 128, and the magnetization map 130 are received. These are each descriptive of a second region of interest of the subject. The first region of interest and the second region of interest comprise an overlapping region of interest that is present in both the first region of interest and the second region of interest.

Then in step 204 pulse sequence commands 132 are received. The pulse sequence commands 132 may be the pulse sequence commands 132 that were used to control a magnetic resonance imaging system to acquire the measured magnetic resonance imaging data 122. Next in step 206 a simulated magnetic resonance image 136 is calculated using a Bloch equation model 134. The B0 map 124, the T1 map 126, the T2 map 128, the magnetization map 130, and the pulse sequence commands 132 are used as input for the Bloch equation model 134. Finally, in step 208 the corrected magnetic resonance image 138 is reconstructed from the measured magnetic resonance imaging data 122 for the overlapping region of interest by solving an inverse problem. The inverse problem comprises an optimization of a cost function and regularization term formed from the simulated magnetic resonance image. The cost function and the regularization term may both be formulated either in image space or in k-space.

Figure 3:
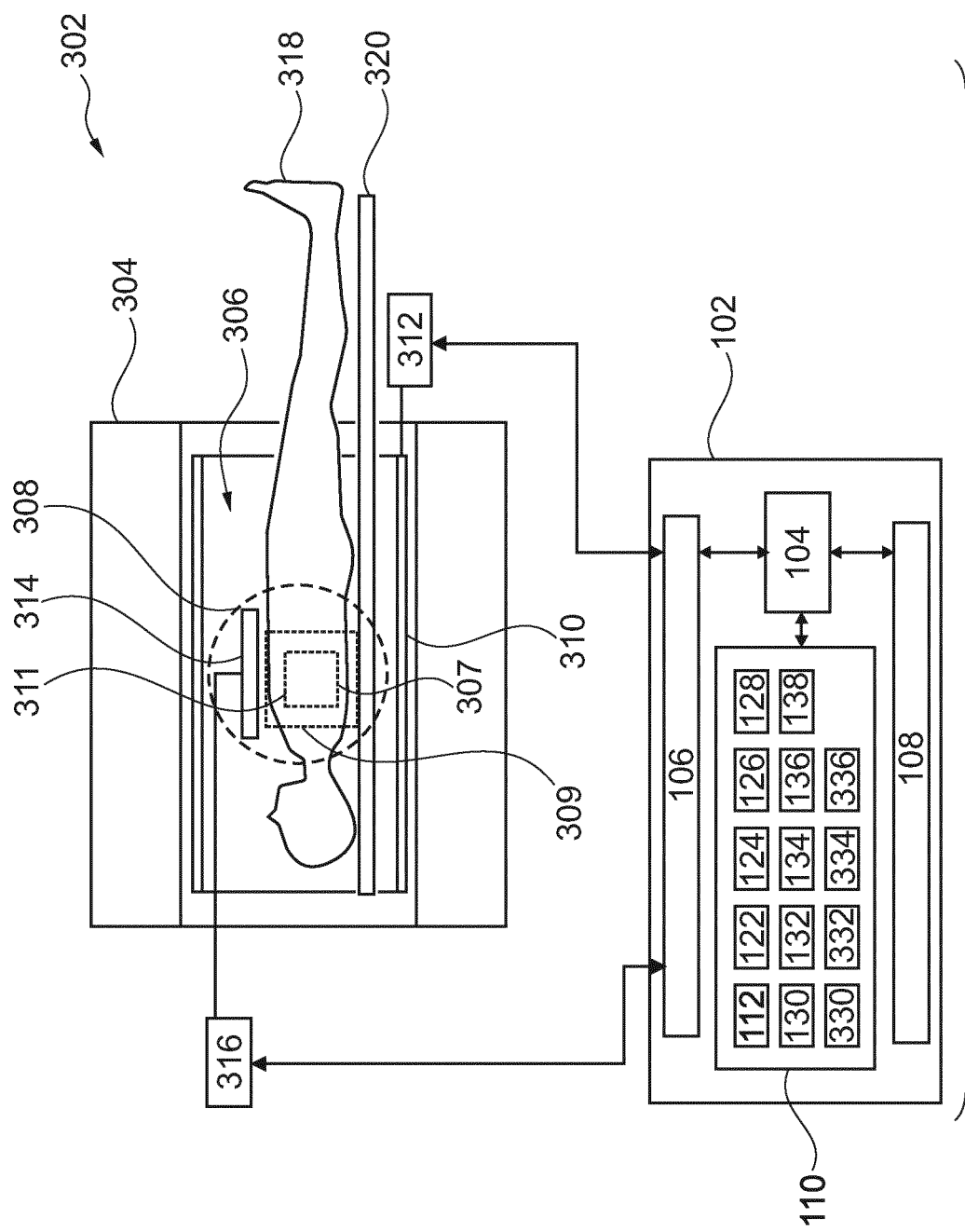
FIG. 3 illustrates a further example of a medical imaging system

FIG. 3 shows a further example of a medical imaging system 300. The medical imaging system 300 is similar to the medical imaging system 100 in FIG. 1 except the system additionally comprises a magnetic resonance imaging system 302.

The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 306 of the cylindrical magnet 304 there is an imaging zone 308 where the magnetic field is strong and uniform enough to perform magnetic resonance imaging. A first region of interest 308 and a second region of interest 309 are shown within the imaging zone 308. The overlapping region of interest between the two is labeled 311. In this case region of interest 307 and 311 are identical. A subject 318 is shown as being supported by a subject support 320 such that at least a portion of the subject 318 is within the imaging zone 308 and the region of interest 309.

Within the bore 306 of the magnet there is also a set of magnetic field gradient coils 310 which is used for acquisition of preliminary magnetic resonance data to spatially encode magnetic spins within the imaging zone 308 of the magnet 304. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements.

The transceiver 316 and the gradient controller 312 are shown as being connected to a hardware interface 106 of computer system 102. The memory 110 is further shown as containing magnetic resonance imaging pulse sequence commands 330. Controlling the magnetic resonance imaging system 302 with the magnetic resonance imaging pulse sequence commands 330 enables the processor 104 to acquire the measured magnetic resonance imaging data 122 for the first region of interest 307. The memory 110 is further shown as containing magnetic resonance fingerprint pulse sequence commands 332. The magnetic resonance fingerprint pulse sequence commands 332 may be used to control the magnetic resonance imaging system 302 to acquire magnetic resonance fingerprint data 334 from the second region of interest 309. The magnetic resonance fingerprint data 334 is shown as also being stored in the memory 110.

The memory 110 is also further shown as containing a magnetic resonance fingerprinting dictionary 336. The magnetic resonance fingerprint data 334 can be used to reconstruct a series of magnetic resonance images. The values or magnitude for a particular voxel comprise a vector which may be compared to the magnetic resonance fingerprinting dictionary 336. This enables the determination of the B0 map 124, the T1 map 126, the T2 map 128, and the magnetization map 130 from the magnetic resonance fingerprint data 334.

Figure 4:
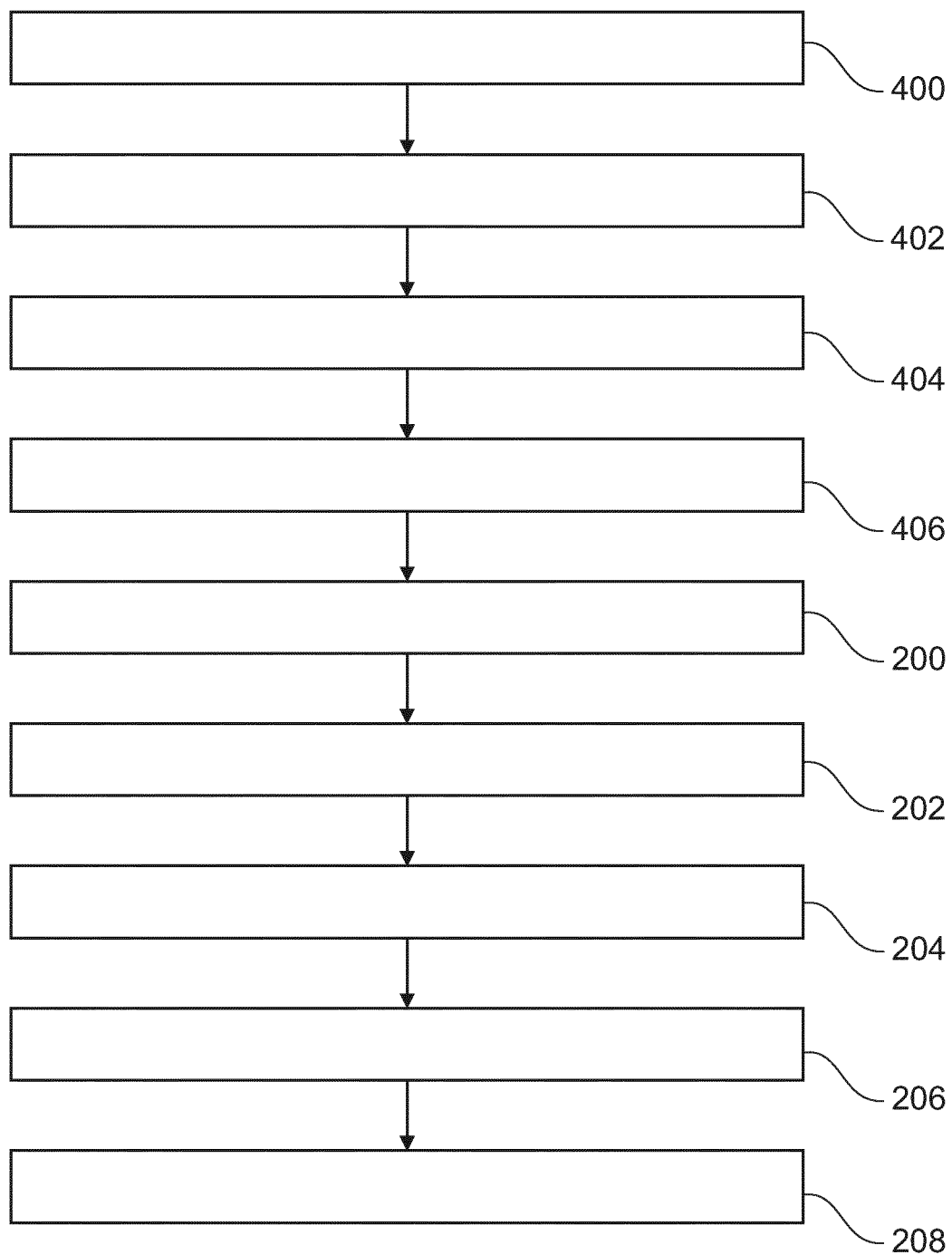
FIG. 4 shows a flow chart which illustrates a method of using the medical imaging system of FIG. 3.

FIG. 4 shows a flowchart which illustrates a method of operating the medical imaging system 300 of FIG. 3. The method steps with step 400. In step 400 the magnetic resonance imaging system 302 is controlled with the magnetic resonance fingerprinting pulse sequence commands 332 to acquire the magnetic resonance fingerprint data 334. Next in step 402 the magnetic resonance imaging system 302 is controlled with the magnetic resonance imaging pulse sequence commands 330 to acquire the measured magnetic resonance imaging data 122. Steps 402 and 400 may be interchanged. Next in step 404 the magnetic resonance fingerprint data is received. It should be noted that the measured magnetic resonance imaging data can be acquired multiple times using different pulse sequences. The B0 map 124, the T1 map 126, the T2 map 128, and the magnetization map 130 from the MRF scan can be reused each time.

The magnetic resonance fingerprint data is descriptive of the second region of interest 309. Then in step 406, the B0 map 124, the T1 map 126, the T2 map 128, and the magnetization map 130 are reconstructed from the magnetic resonance fingerprint data 334 using the magnetic resonance fingerprinting dictionary 336. After step 406 is performed the method then proceeds to steps 200-208 as is illustrated in FIG. 2.

The output of a (potentially low-resolution) Magnetic Resonance Fingerprinting (MRF) prescan can be used to determine various spatially dependent values such as the B0 map, the T1 map, the T2 map, and magnetization. In turn these values can be used to simulate the acquisition of magnetic resonance imaging data.

This enables the generation of synthetic data (136) simulated magnetic resonance image, matching a subsequent clinical scan (image reconstructed from the measured magnetic resonance imaging data 122) in terms of contrast. This synthetic data can be used as a source of prior knowledge to improve the regularization in the reconstruction of the clinical data (e.g. regularization in SENSE reconstruction or for a SENSE unfolding problem).

MR Reconstruction by solving inverse problems is becoming more popular. Some relevant examples are for SENSE reconstruction and Compressed SENSE reconstruction. In some cases, the inverse problem is ill-posed and/or ill conditioned. These ill posed problems may be solved by using prior knowledge that is included in the inverse problem as a form of regularization.

In some cases, it would be helpful if the source of prior knowledge was matching the clinical scan in terms of image contrast. This would further constrain the image reconstruction towards the optimal result.

For example, it is considered here the problem of overlapping areas in EPI distortion correction. This is an ill-posed problem and regularization could help in finding the best possible outcome. This is illustrated in FIGS. 5 to 10 below.

Figure 5:
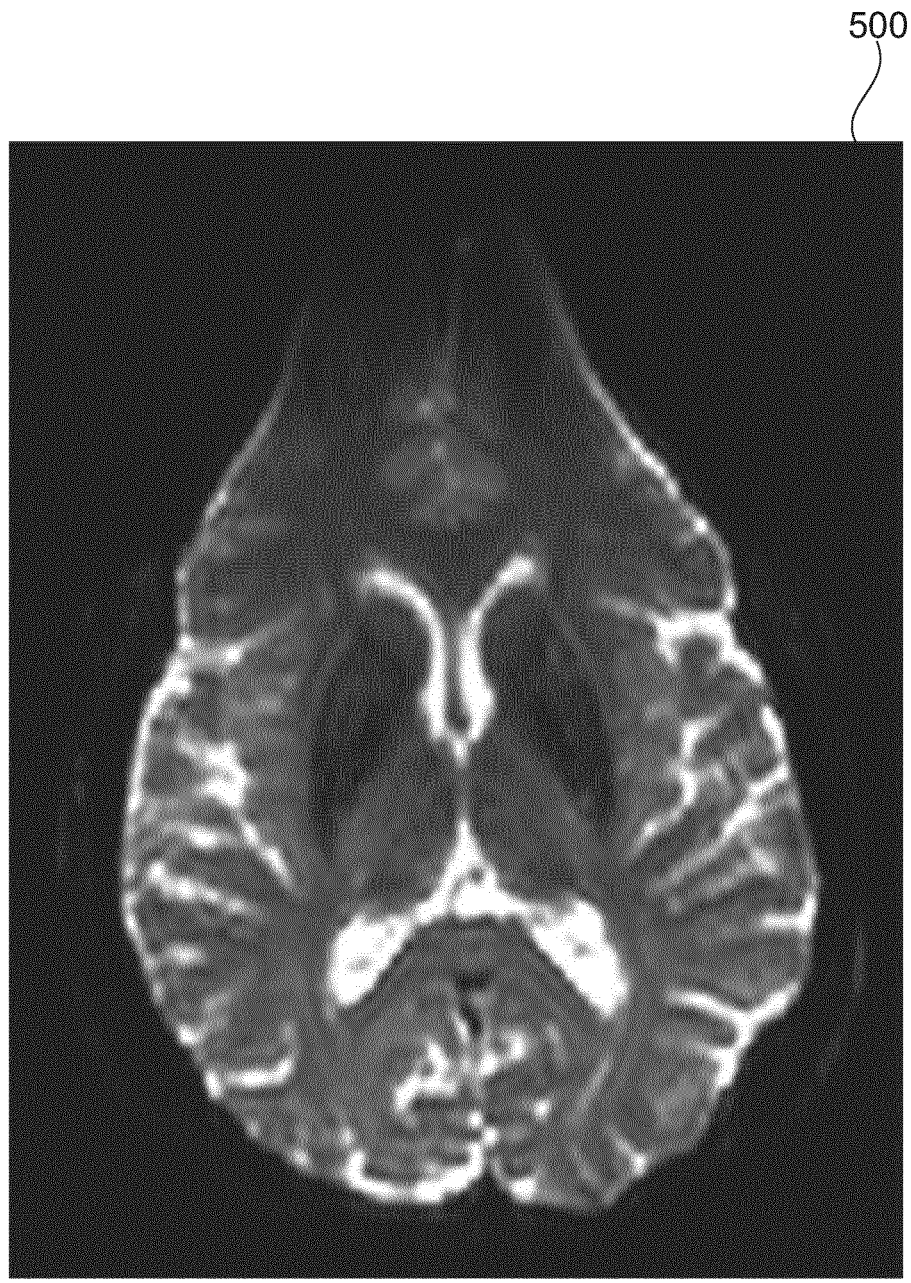
FIG. 5 shows a distorted EPI magnetic resonance image.

FIGS. 5-10 are used to show different examples of correcting a distortion within an EPI or echo planar imaging image. FIG. 5 shows an EPI image 500 which contains distortion.

Figure 6:
FIG. 6 shows a corrected version of FIG. 5.

FIG. 6 shows an EPI image 600 with a distortion correction that uses no prior knowledge. In FIG. 6, the system is ill posed and tissue splitting is generated in the frontal area.

Figure 7:
FIG. 7 shows a further corrected version of FIG. 5.

FIG. 7 shows an EPI image 700 with distortion correction that uses a regularization based on a water image from a pre-scan or alternative scan. In FIG. 700 it can still be seen that there is a region with very visible distortion. In this Fig.

the splitting in the frontal area is reduced, by using prior knowledge of where the water signal is expected to be present.

Figure 8:
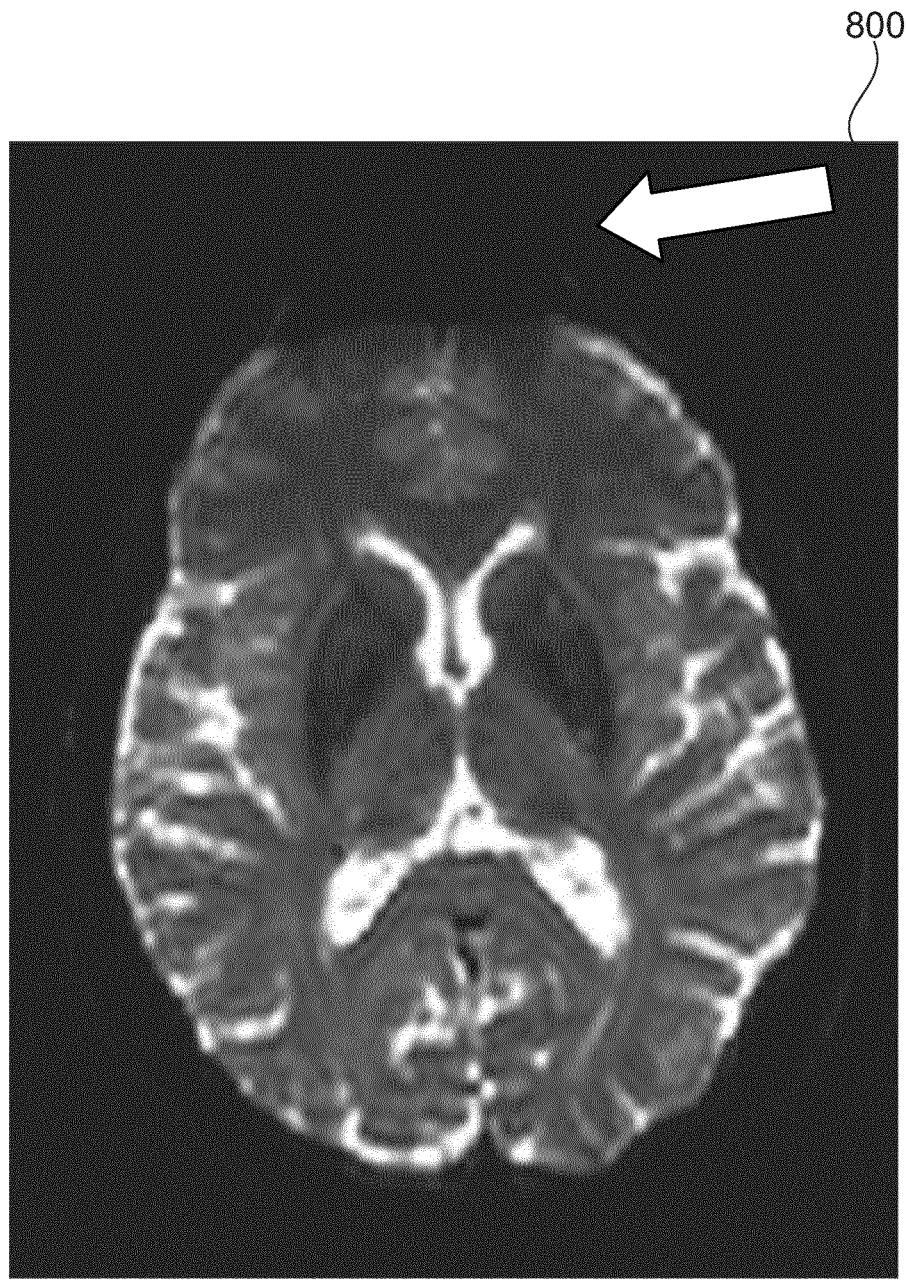
FIG. 8 shows a further corrected version of FIG. 5.

FIG. 8 shows a further EPI image 800 with a distortion correction that uses a regularization based on a T2 weighted image with a contrast similar to the original EPI image 500. The EPI image 800 is according to an example as disclosed herein.

Figure 9:
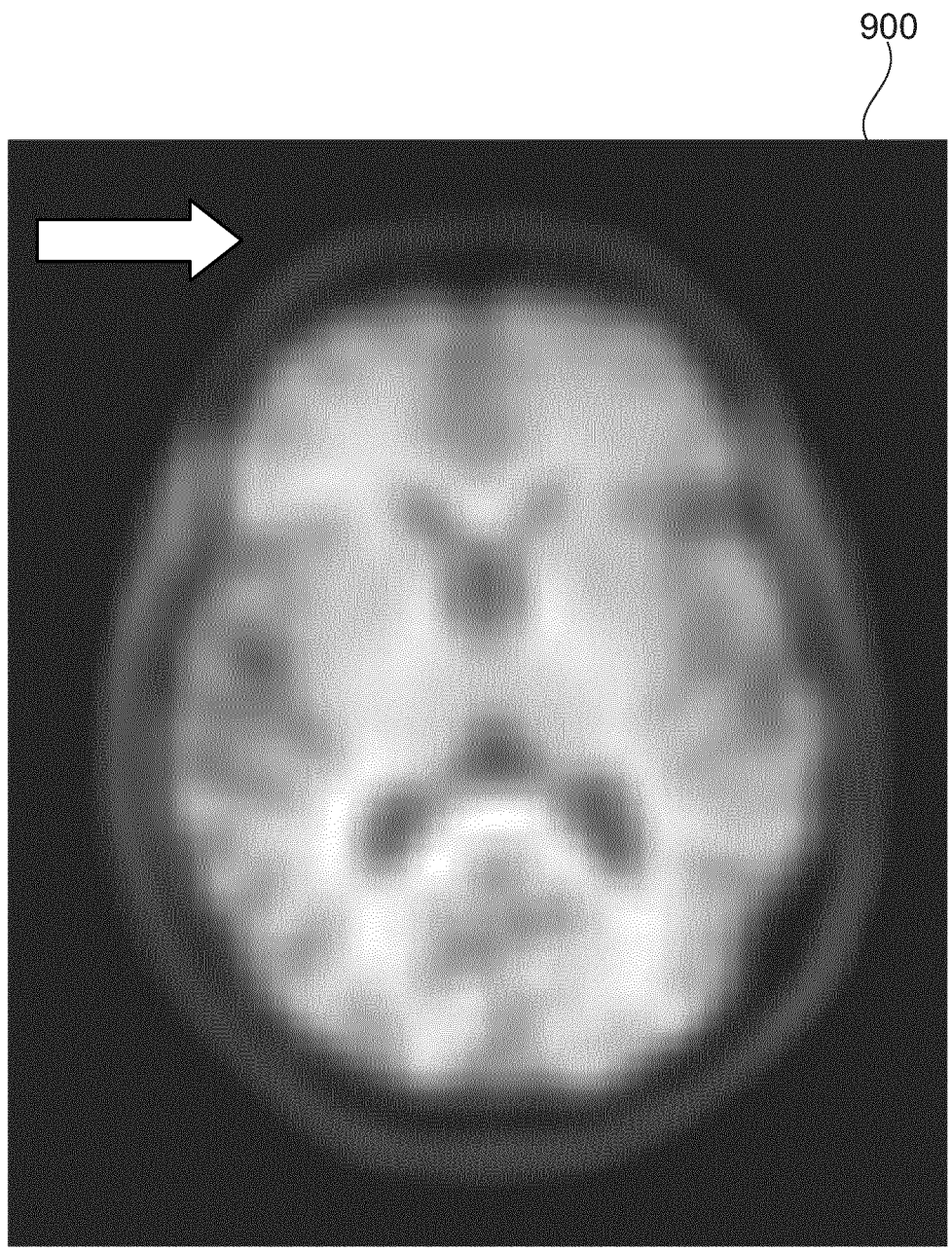
FIG. 9 shows a regularization image used for the reconstruction of FIG. 7.
Figure 10:
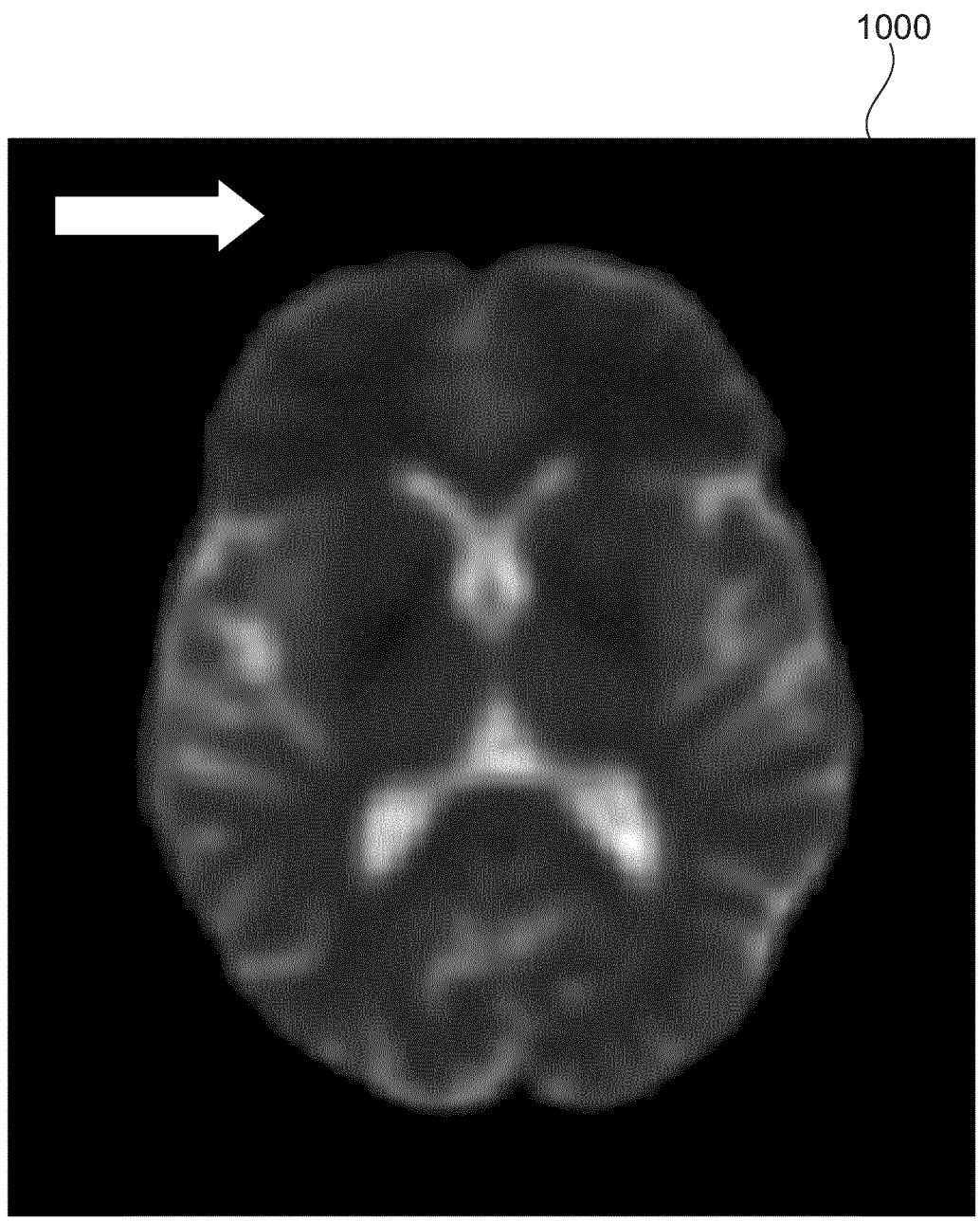
FIG. 10 shows a regularization image used for the reconstruction of FIG. 8.

FIG. 9 shows a regularization image 900 that was used for the example illustrated in FIG. 7. FIG. 10 shows a further regularization image 1000 that was used for the correction in FIG. 8 of image 800. In FIG. 10, the suppression of the signal from the skin is able to constrain better the solution of the EPI distortion problem, as is see in FIG. 8. In FIG. 9 a T2 weighted image with a contrast similar to the original image was used.

Comparing FIGS. 7 and 8 it can be seen readily that there is less distortion in FIG. 800 than in FIG. 700. FIG. 800 is an example of the benefit of using the methods and techniques disclosed herein. It is evident that in the last case the prior knowledge is able to constrain the solution more of the EPI distortion problem, which is an ill-posed inverse problem.

Even if this example is explicit for EPI distortion correction, this is a common feature of every reconstruction based on the solution of an inverse problem (whether the reconstruction is Compressed Sensing, Compressive Sensing or others).

The acquisition of an image for every possible contrast to be used on the corresponding inverse problem is however impractical, because it would require a lot of acquisitions.

Disclosed is a method to obtain a source of prior knowledge that is matching in contrast with the clinical scan, by avoiding to acquire an image for every possible contrast.

Some examples may use a Magnetic Resonance Fingerprinting (MRF) acquisition of a (possibly low resolution) image on the same anatomy to generate the source of prior knowledge.

This acquisition can be a fast 3D acquisition to be used at the beginning of the exam, in the form of a prescan. From such a prescan information about the T1, T2, the magnetization values, and the B0 map spatial distribution can be extracted.

These values can be used later to generate a synthetic image similar in contrast to the image that is acquired in a subsequent scan.

This synthetic image can be used as a source of prior knowledge in the reconstruction of the second scan.

Some examples may be divided into two main parts:
1. MRF prescan acquisition and reconstruction. Derivation of T1, T2* and magnetization values followed by storage of this information in the database
    this is not different from a conventional MRF reconstruction.
2. For every subsequent clinical scan:
   a) Get the B0, T1, T2 and magnetization values from the database
   b) Perform a multi planar reformatting (MPR) operation to resample the prescan data on the geometry of the clinical scan
   c) Use information retrieved at the point b) together to the scan acquisition parameters (e.g. echo time, repetition time, flip angle and other sequence parameters) to generate a synthetic image using the Bloch equations.
   d) Use this image as a source of prior knowledge for the reconstruction of the clinical data. This is in general framed as an inverse problem. Given a generic model f for the relationship between the image x and the data y:

$$y = f(x)$$

The inverse problem is trying to produce an estimate of x starting from the data y. This is typically achieved by minimizing a cost function composed by a data consistency function C and some regularization terms $R_i$:

$$\hat{x} = \operatorname*{argmin}_x \left[ C(f(x) - y) + \sum_i R_i(x) \right]$$

In this framework the prior knowledge information on the signal localization can be included as a regularization term:

$$\hat{x} = \operatorname*{argmin}_x \left[ C(f(x) - y) + \left\| \frac{x}{\alpha |x_p|} \right\|_2^2 + \sum_i R_i(x) \right]$$

Here $x_p$ is the image containing the prior info (the synthetic image generated at point 2c, and $\alpha$ is a general scaling factor. In this equation the general summation of regularization terms is kept because there could be different sources of prior knowledge.

The following three examples are provided to detail on three different implementations (and aims) of the step 2d:
1. EPI Geometry Correction:
In this case the problem is modelled as a linear system, relating the distorted image y with the undistorted image x. If we denote with D the distortion operator, the model is the following:

$$y = Dx$$

Distortion correction with the proposed method would be achieved by solving the following:

$$\operatorname*{argmin}_x \left[ \|Dx - y\|_2^2 + \left\| \frac{x}{\alpha |x_p|} \right\|_2^2 \right]$$

Here $x_p$ is the image obtained as described previously, that tries to mimic the contrast of the target EPI scan (whether it is an fMRI, perfusion, or diffusion image)
2. Parallel Imaging (i.e. SENSE) Unfolding:
In this case the problem is modelled as a linear system, relating the folded channel images y with the original image x. If we denote with F the folding operator, and with S the coil sensitivity map weighting, the model is the following:

$$y = FSx$$

Parallel Imaging unfolding with the proposed method would be achieved by solving the following:

$$\operatorname*{argmin}_x \left[ \|FSx - y\|_2^2 + \left\| \frac{x}{\alpha |x_p|} \right\|_2^2 \right]$$

Here $x_p$ is the image obtained as described previously, that tries to mimic the contrast of the target clinical scan (any scan where currently Parallel Imaging could be applied)
3. Compressed Parallel Imaging (i.e. Compressed SENSE):

Also in this case a linear model represents the data acquisition:

$$y = ASx$$

Here A represents the under sampled Fourier transform. The reconstruction is obtained as:

$$\operatorname*{argmin}_{x}\left[\|ASx - y\|_2^2 + \left\|\frac{x}{\alpha|x_p|}\right\|_2^2 + \beta\|\Psi x\|_1\right]$$

Where $\Psi$ represents transformation in a sparse domain (e.g. Wavelet transform).

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical imaging system
102 computer
104 processor
106 hardware interface
108 user interface
110 memory
120 machine executable instructions
122 measured magnetic resonance imaging data
124 B0 map
126 T1 map
128 T2 map
130 magnetization map
132 pulse sequence commands
134 Bloch equation model
136 simulated magnetic resonance image
138 corrected magnetic resonance image
200 receive measured magnetic resonance imaging data descriptive of a first region of interest of a subject
202 receive a B0 map, a T1 map, a T2 map, and a magnetization map each descriptive of a second region of interest of the subject
204 receive a pulse sequence commands configured for controlling a magnetic resonance imaging system to acquire the measured magnetic resonance imaging data
206 calculate a simulated magnetic resonance image of the overlapping region of interest using at least the B0 map, the T1 map, the T2 map, the magnetization map, and the pulse sequence commands as input to a Bloch equation model
208 reconstruct a corrected magnetic resonance image from the measured magnetic resonance imaging data for the overlapping region of interest by solving an inverse problem
300 medical imaging system
302 magnetic resonance imaging system
304 magnet
306 bore of magnet
307 first region of interest
308 imaging zone
309 second region of interest
310 magnetic field gradient coils
311 overlapping region of interest
312 magnetic field gradient coil power supply
314 radio-frequency coil
316 transceiver
318 subject
320 subject support
330 magnetic resonance imaging pulse sequence commands
332 magnetic resonance fingerprint pulse sequence commands
334 magnetic resonance fingerprint data
336 magnetic resonance fingerprinting dictionary
400 control the magnetic resonance imaging system with the magnetic resonance fingerprinting pulse sequence commands to acquire the magnetic resonance fingerprint data
402 control the magnetic resonance imaging system with the magnetic resonance imaging pulse sequence commands to acquire the magnetic resonance imaging data
404 receive magnetic resonance fingerprint data acquired according to a magnetic resonance fingerprinting protocol, wherein the magnetic resonance fingerprint data is descriptive of the second region of interest
406 reconstruct at least one of the B0 map, the T1 map, the T2 map, and the magnetization map from the magnetic resonance fingerprint data using a magnetic resonance fingerprinting dictionary according to the magnetic resonance imaging protocol
500 EPI image containing distortion
600 EPI image with distortion correction—no prior knowledge
700 EPI image with distortion correction using regularization based on water image from DIXON prescan
800 EPI image with distortion correction using regularization based on T2 weighted image with a contrast similar to the EPI scan
900 regularisation image for image 700
1000 regularisation image for image 800

The invention claimed is:

1. A medical imaging system, wherein the medical imaging system comprises:
a memory storing machine executable instructions; and
a processor for controlling the medical imaging system, wherein execution of the machine executable instructions causes the processor to:
receive measured magnetic resonance imaging data descriptive of a first region of interest of a subject;
receive a $B_0$ map and at least one of a transverse relaxation map and a longitudinal relaxation map, preferably both a T1 map, a T2 map (128) and/or a T2* map, and a magnetization map each descriptive of a second region of interest of the subject, wherein the first region of interest of the subject and the second region of interest of the subject both comprise an overlapping region of interest;

receive pulse sequence commands configured for controlling a magnetic resonance imaging system to acquire the measured magnetic resonance imaging data;

calculate a simulated magnetic resonance image of the overlapping region of interest using at least the B0 map, and at least one of a transverse relaxation map and a longitudinal relaxation map, preferably both the T1 map, the T2 map, and/or T2* map, the magnetization map, and the pulse sequence commands as input to a Bloch equation model; and reconstruct a corrected magnetic resonance image from the measured magnetic resonance imaging data for the overlapping region of interest by solving an inverse problem, wherein the inverse problem comprises an optimization of a cost function and a regularization term formed from the simulated magnetic resonance image.

2. The medical imaging system of claim 1, wherein the regularization term is a Tikhonov regularization, wherein the Tikhonov regularization comprises an estimate of a first image magnitude calculated from the corrected magnetic resonance imaging data divided by a second image magnitude calculated from the simulated magnetic resonance image for each voxel of the overlapping region of interest.

3. The medical imaging system of claim 1, wherein the inverse problem is an Echo Planar Imaging geometry correction problem.

4. The medical imaging system of claim 3, wherein the cost function comprises an Euclidian norm of a difference between a distortion operator times the corrected magnetic resonance imaging data and the measured magnetic resonance image.

5. The medical imaging system of claim 1, wherein the inverse problem is a parallel imaging unfolding problem.

6. The medical imaging system of claim 5, wherein the cost function comprises an Euclidian norm of a difference between a folding operator times a coil sensitivity map times the corrected magnetic resonance image and the measured magnetic resonance image.

7. The medical imaging system of claim 1, wherein the inverse problem is a compressive sensing in combination with a parallel imaging unfolding problem.

8. The medical imaging system of claim 7, wherein the cost function comprises an Euclidian norm of a difference of an under sampled Fourier transform times a coil sensitivity map times the corrected magnetic resonance image and the measured magnetic resonance image.

9. The medical imaging system of claim 1, wherein the B0 map, the T1 map, the T2 map, and the magnetization map have a first resolution, wherein the magnetic resonance imaging has a second resolution, wherein the first resolution is lower than the second resolution.

10. The medical imaging system of claim 1, wherein execution of the machine executable instructions further causes the processor to perform a multiplanar reformatting of the B0 map, the T1 map, the T2 map, and the magnetization map to make a geometric match to the measured magnetic resonance image before calculating the simulated magnetic resonance image.

11. The medical imaging system of claim 1, wherein execution of the machine executable instructions further causes the processor to:

receive magnetic resonance fingerprint data acquired according to a magnetic resonance fingerprinting protocol, wherein the magnetic resonance fingerprint data is descriptive of the second region of interest; and reconstruct at least one of the B0 map, the T1 map, the T2 map, and the magnetization map from the magnetic resonance fingerprint data using a magnetic resonance fingerprinting dictionary according to the magnetic resonance imaging protocol.

12. The medical imaging system of claim 11, wherein the medical imaging system further comprises the magnetic resonance imaging system, wherein the memory further contains magnetic resonance imaging pulse sequence commands configured for acquiring the measured magnetic resonance imaging data, wherein the memory further contains magnetic resonance fingerprinting pulse sequence commands configured for acquiring the magnetic resonance fingerprint data according to the magnetic resonance fingerprinting protocol, wherein execution of the machine executable instructions further cause the processor to:

control the magnetic resonance imaging system with the magnetic resonance fingerprinting pulse sequence commands to acquire the magnetic resonance fingerprint data; and control the magnetic resonance imaging system with the magnetic resonance imaging pulse sequence commands to acquire the measured magnetic resonance imaging data.

13. A non-transitory computer program product comprising machine executable instructions for execution by a processor controlling a medical imaging system, wherein execution of the machine executable instructions causes the processor to:

receive measured magnetic resonance imaging data descriptive of a first region of interest of a subject;

receive a $B_0$ map, and at least one of a transverse relaxation map and a longitudinal relaxation map, preferably both a T1 map, a T2 map (128) and/or a T2* map, and a magnetization map each descriptive of a second region of interest of the subject, wherein the first region of interest of the subject and the second region of interest of the subject both comprise an overlapping region of interest;

receive pulse sequence commands configured for controlling a magnetic resonance imaging system to acquire the measured magnetic resonance imaging data;

calculate a simulated magnetic resonance image of the overlapping region of interest using at least the B0 map, and at least one of a transverse relaxation map and a longitudinal relaxation map, preferably both the T1 map, the T2 map, and/or T2*map the magnetization map, and the pulse sequence commands as input to a Bloch equation model; and reconstruct a corrected magnetic resonance image from the measured magnetic resonance imaging data for the overlapping region of interest by solving an inverse problem, wherein the inverse problem comprises an optimization of a cost function and a regularization term formed from the simulated magnetic resonance image.

14. A method of operating a medical imaging system, wherein the method comprises:

receiving measured magnetic resonance imaging data descriptive of a first region of interest of a subject;

receiving a B0 map, and at least one of a transverse relaxation map and a longitudinal relaxation map, preferably both a T1 map, a T2 map and/or a T2* map, and a magnetization map each descriptive of a second region of interest of the subject, wherein the first region of interest of the subject and the second region of interest of the subject both comprise an overlapping region of interest;

receiving pulse sequence commands configured for controlling a magnetic resonance imaging system to acquire the measured magnetic resonance imaging data;

calculating a simulated magnetic resonance image of the overlapping region of interest using at least the $B_0$ map, and at least one of a transverse relaxation map and a longitudinal relaxation map, preferably both the T1 map, the T2 map, and/or a T2* map, the magnetization map, and the pulse sequence commands as input to a Bloch equation model; and reconstructing a corrected magnetic resonance image from the measured magnetic resonance imaging data for the overlapping region of interest by solving an inverse problem, wherein the inverse problem comprises an optimization of a cost function and a regularization term formed from the simulated magnetic resonance image.

* * * * *